US012667597B2

(12) United States Patent (10) Patent No.: US 12,667,597 B2

Malanchin et al. (45) Date of Patent: Jun. 30, 2026

(54) PROBIOTIC COMPOSITIONS USEFUL IN THE PREVENTION AND/OR TREATMENT OF GASTROINTESTINAL DISORDERS

(71) Applicant: SYNBALANCE SRL, Origgio (IT)

(72) Inventors: Rosella Malanchin, Origgio (IT); Cristiana Piangiolino, Origgio (IT); Silvia Castegnaro, Origgio (IT); Federica Carlomagno, Origgio (IT); Chiara Pesciaroli, Origgio (IT)

(73) Assignee: SYNBALANCE SRL, Origgio (IT)

( * ) Notice: Subject to any disclaimer, the term of this patent is extended or adjusted under 35 U.S.C. 154(b) by 329 days.

(21) Appl. No.: 18/279,040

(22) PCT Filed: Mar. 29, 2022

(86) PCT No.: PCT/IB2022/052881

§ 371 (c)(1),
(2) Date: Aug. 25, 2023

(87) PCT Pub. No.: WO2022/208341

PCT Pub. Date: Oct. 6, 2022

(65) Prior Publication Data

US 2024/0131090 A1     Apr. 25, 2024
US 2024/0226200 A9     Jul. 11, 2024

(30) Foreign Application Priority Data

Mar. 29, 2021     (IT) ......................... 102021000007682

(51) Int. Cl.
*A61K 35/747*     (2015.01)
*A61K 35/745*     (2015.01)
*A61P 1/00*      (2006.01)

(52) U.S. Cl.
CPC .......... *A61K 35/747* (2013.01); *A61K 35/745* (2013.01); *A61P 1/00* (2018.01)

(58) Field of Classification Search
CPC ........ A61K 35/747; A61K 35/745; A61P 1/00
See application file for complete search history.

(56) References Cited

U.S. PATENT DOCUMENTS 9,579,353 B2     2/2017  Olmstead
2017/0165303 A1*  6/2017  Olmstead ................ A61P 27/16
2018/0296582 A1*  10/2018  von Maltzahn ...... A61K 31/192

FOREIGN PATENT DOCUMENTS

AU     2015100952 A4     8/2015
AU     2016100865 A4     7/2016
IT      201900014388 A1    2/2021

OTHER PUBLICATIONS

"Nexabiotic Compare Probiotics", Internet Citation, Jan. 1, 2011, pp. 1-9, XP009516416, retrieved from the Internet: URL:https://nexabiotic.com/compareprobiotics.

Mezzasalma et al., "A Randomized, Double-Blind, Placebo-Controlled Trial: The Efficacy of Multispecies Probiotic Supplementation in Alleviating Symptoms of Irritable Bowel Syndrome Associated with Constipation", BioMed Research International, 2016, vol. 2016, Article ID 4740907, 10 pages, http://downloads.hindawi.com/journals/omri/2016/4740907.pdf [retrieved on Dec. 8, 2021].

Cicero et al., "Impact of a short-term synbiotic supplementation on metabolic syndrome and systemic inflammation in elderly patients: a randomized placebo-controlled clinical trial", European Journal of Nutrition, 2021, 60: 655-663.

Presti et al., "Evaluation of the probiotic properties of new Lactobacillus and Bifidobacterium strains and their in vitro effect", Appl Microbiol Biotechnol, 2015, 99: 5613-5626.

* cited by examiner

*Primary Examiner* — Ruth A Davis

(74) *Attorney, Agent, or Firm* — James S. Keddie; Bozicevic, Field & Francis LLP

(57)     ABSTRACT

In particular, this invention refers to a composition comprising a probiotic combination comprising: a) at least one strain of the genus *Lactobacillus* selected from the species *Lactobacillus plantarum*; and c) at least one strain belonging to the genus *Bifidobacterium* selected from the species *Bifidobacterium lactis, Bifidobacterium longum, Bifidobacterium infantis*; wherein said composition is for use in a method for the prevention and/or treatment of chronic inflammatory bowel disease (Inflammatory Bowel Disease IBD).

10 Claims, 1 Drawing Sheet

PROBIOTIC COMPOSITIONS USEFUL IN THE PREVENTION AND/OR TREATMENT OF GASTROINTESTINAL DISORDERS

CROSS-REFERENCE TO RELATED APPLICATIONS

This application is a § 371 national phase of International Application No. PCT/IB2022/052881, filed on Mar. 29, 2022, which claims the benefit of Italian Application No. 102021000007682, filed on Mar. 29, 2021, all of which applications are incorporated by reference herein.

TECHNICAL FIELD OF THE INVENTION

The present invention refers to compositions comprising a probiotic combination comprising:
- a) at least one strain belonging to the genus *Lactobacillus* selected from the species *Lactobacillus plantarum, Lactobacillus acidophilus, Lactobacillus helveticus* and *Lactobacillus gasseri*; and/or
- b) at least one other strain belonging to the genus *Lactobacillus* selected from the species *Lactobacillus rhamnosus, Lactobacillus reuteri* and *Lactobacillus fermentum*; and/or
- c) at least one strain belonging to the genus *Bifidobacterium* selected from the species *Bifidobacterium* lactis, *Bifidobacterium* breve, *Bifidobacterium* longum, *Bifidobacterium infantis*, for use in the prevention and/or treatment of gastrointestinal disorders.

In particular, the present invention refers to a composition comprising a probiotic combination comprising:
- a) at least one strain belonging to the genus *Lactobacillus* selected from the species *Lactobacillus plantarum*; and
- c) at least one strain belonging to the genus *Bifidobacterium* selected from the species *Bifidobacterium* lactis, *Bifidobacterium longum, Bifidobacterium infantis*; wherein said composition is for use in a method for the prevention and/or treatment of chronic inflammatory bowel disease (Inflammatory Bowel Disease IBD).

STATE OF THE ART

Intestinal dysbiosis is a condition of alteration of the balance of the microbial ecosystem resident in the human intestinal tract. This imbalance also affects the immune system, considering that 70% of immune cells reside in the intestinal tract due to the presence of intestinal lymphoid tissue (GALT). Intestinal dysbiosis can be caused by multiple factors such as poor nutrition, difficulty in taking food, food intolerances, antibiotic therapies or travel bacterial infections; or it may be related to chronic inflammatory bowel disease, obesity and cancer.

Concurrently with advancing age, a series of immune-metabolic deficits are added, as a lower nutrients absorption or more disabling conditions, linked to para-physiological conditions such as chewing and swallowing problems. Related to the manifestation of these co-morbidities, the intestinal microbiota also undergoes alterations that negatively affect the already compromised clinical picture.

Food intolerances are disorders that occur after food ingestion. These are adverse reactions to food that depend on the body's difficulty in metabolizing a given food or component. The best known are lactose and gluten intolerances. Symptoms often associated with intolerances are intestinal-like such as diarrhoea, abdominal pain or swelling, bloating or digestive problems in general. To date, there are no known effective therapies to stop these adverse reactions, other than to avoid the intake of the specific food.

"Traveler's diarrhoea" means a condition characterized by variable intensity diarrhoea, which usually affects people traveling through countries with precarious health conditions, in which it is possible to ingest contaminated food. It is a very common situation, affecting 35% of travellers. The main causes associated with this phenomenon are bacterial, viral and protozoal infections. In addition, the stress of travelling, changing habits and diet can also affect the development of this syndrome. There is currently no cure available to prevent this phenomenon, but proper food hygiene is recommended, avoiding contact with the responsible microorganisms.

Antibiotic therapy is known to have side effects, such as diarrhoea. This is because taking antibiotics during bacterial infections tends to eliminate all microorganisms present in the intestines, both pathogenic and non-pathogenic, causing an alteration of the intestinal balance. In addition, some antibiotic drugs, such as erythromycin, also have prokinetic activity, which can modulate intestinal motility causing a diarrheal event.

Chronic intestinal diseases (Irritable Bowel Disease or IBD) are defined as idiopathic, whose cause is unknown, and the pathogenic hypothesis refers to an abnormal immunological reaction by the intestine to antigens. This immunological imbalance can arise due to an altered interaction between the individual's genetic factors and environmental factors. Crohn's disease and ulcerative rettocolitis belong to this family. It is estimated that in Italy about 200,000 people aged between 15 and 45 years are affected. Both pathologies are characterized by a chronic or recurrent course, and occur with periods of latency alternating with phases of exacerbation.

The symptoms characterizing these two conditions are different, for Crohn's disease diarrhoea is very frequent, associated with localized abdominal pain; while ulcerative rettocolitis often occurs with bloody diarrhoea associated with "tenesmus" (feeling of incomplete evacuation) and sometimes anemia. For this type of disease, medical therapy aims to induce clinical remission of the disease and to keep patients free from exacerbations.

Please note that IBD and IBS (irritable bowel syndrome) are two different conditions and should not be confused with each other. IBD is a physical disease characterized by chronic intestinal inflammation with periodic exacerbations. In IBS, on the other hand, there is no "full-blown" pathology and the symptoms are the result of a poor functioning of the digestive tract. It seems that differences in the composition of the gut microbiota can be used to distinguish people with inflammatory bowel disease (IBD) from those with irritable bowel syndrome (IBS). This was reported by researchers in the journal *Science Translational Medicine*. The study was conducted by Arnau Vich Vila, Floris Imhann and Valerie Collij at the University of Groningen and the University Medical Centre Groningen in the Netherlands.

In view of the above, there is still a need to identify effective alternative compositions for the prevention and/or treatment of gastrointestinal disorders, in particular effective, well-tolerable and easy-to-administer compositions for use, for all categories of subjects, in a method for the prevention and/or treatment of chronic inflammatory bowel disease IBD, such as Crohn's disease and ulcerative colitis.

3

Figure 2:
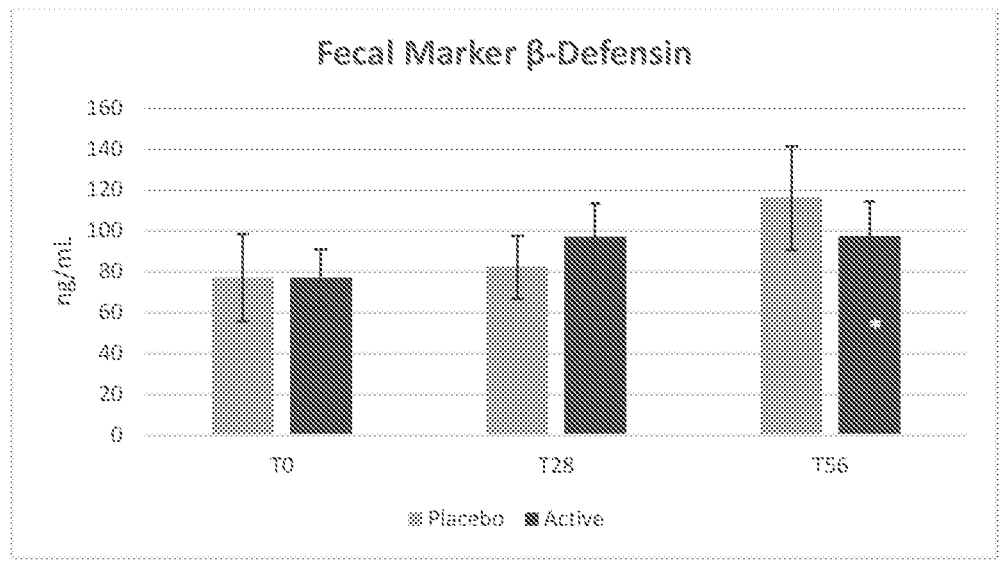

FIG. 2 shows the increase of the β-defensin 2 fecal marker in both the active and placebo groups during the three checkpoints.

SUMMARY OF THE INVENTION

The present invention refers to compositions comprising a probiotic combination comprising:
- a) at least one strain belonging to the genus *Lactobacillus* selected from the species *Lactobacillus plantarum, Lactobacillus acidophilus, Lactobacillus helveticus* and *Lactobacillus* gasseri; and/or
- b) at least one other strain belonging to the genus *Lactobacillus* selected from the species *Lactobacillus rhamnosus, Lactobacillus reuteri* and *Lactobacillus fermentum*; and/or
- c) at least one strain belonging to the genus *Bifidobacterium* selected from the species *Bifidobacterium* lactis, *Bifidobacterium* breve, *Bifidobacterium* longum, *Bifidobacterium infantis*; for use in the prevention and/or treatment of gastrointestinal disorders.

In particular, this invention refers to a composition comprising a probiotic combination comprising:
- a) at least one strain belonging to the genus *Lactobacillus* selected from the species *Lactobacillus plantarum*; and
- c) at least one strain belonging to the genus *Bifidobacterium* selected from the species *Bifidobacterium* lactis, *Bifidobacterium* longum, *Bifidobacterium infantis*; wherein said composition is for use for a method for the prevention and/or treatment of chronic inflammatory bowel disease (Inflammatory Bowel Disease IBD).

DETAILED DESCRIPTION OF THE INVENTION

This invention refers to compositions comprising a probiotic combination comprising:
- a) at least one strain belonging to the genus *Lactobacillus* selected from the species *Lactobacillus plantarum* (also known as Lactiplantibacillus *plantarum*), *Lactobacillus acidophilus, Lactobacillus helveticus* and *Lactobacillus* gasseri; and/or
- b) at least one other strain belonging to the genus *Lactobacillus* selected from the species *Lactobacillus rhamnosus* (also known as: *Lacticaseibacillus rhamnosus*), *Lactobacillus reuteri* (also known as: *Limosilactobacillus reuteri*) and *Lactobacillus fermentum* (also known as: *Limosilactobacillus fermentum*); and/or
- c) at least one strain belonging to the genus *Bifidobacterium* selected from the species *Bifidobacterium* lactis, *Bifidobacterium* breve, *Bifidobacterium* longum, *Bifidobacterium infantis*; for use in the prevention and/or treatment of gastrointestinal disorders, in particular for use, for all categories of subjects, in a method for the prevention and/or treatment of chronic inflammatory bowel disease IBD, such as Crohn's disease and ulcerative colitis.

In particular, this invention refers to a composition comprising a probiotic combination comprising:
- a) at least one strain of the genus *Lactobacillus* selected from the species *Lactobacillus plantarum*; and
- c) at least one strain belonging to the genus *Bifidobacterium* selected from the species *Bifidobacterium* lactis, *Bifidobacterium* longum, *Bifidobacterium infantis*; wherein said composition is for use in a method for the prevention and/or treatment of chronic inflammatory bowel disease (Inflammatory Bowel Disease IBD), in particular for use, for all categories of subjects, in a method for the prevention and/or treatment of chronic inflammatory bowel disease IBD, such as Crohn's disease and ulcerative colitis.

It has surprisingly been found that compositions comprising a probiotic combination comprising:
- a) at least one strain of the genus *Lactobacillus* selected from the species *Lactobacillus plantarum, Lactobacillus acidophilus, Lactobacillus helveticus* and *Lactobacillus* gasseri; and/or
- b) at least one other strain belonging to the genus *Lactobacillus* selected from the species *Lactobacillus rhamnosus, Lactobacillus reuteri* and *Lactobacillus fermentum*; and/or
- c) at least one strain belonging to the genus *Bifidobacterium* selected from the species *Bifidobacterium* lactis, *Bifidobacterium* breve, *Bifidobacterium* longum, *Bifidobacterium infantis*, are effective in the prevention and/or treatment of gastrointestinal disorders.

According to a first preferred aspect of the invention, the compositions include a probiotic combination comprising:
- a) at least one strain of the genus *Lactobacillus* selected from the species *Lactobacillus plantarum, Lactobacillus acidophilus, Lactobacillus helveticus* and *Lactobacillus* gasseri; and
- c) at least one strain belonging to the genus *Bifidobacterium* selected from the species *Bifidobacterium* lactis, *Bifidobacterium* breve, *Bifidobacterium* longum, *Bifidobacterium infantis*; in the prevention and/or treatment of gastrointestinal disorders.

A composition for use according to the invention includes a probiotic combination comprising: a strain of *Lactobacillus plantarum* in combination with a strain of *Bifidobacterium* lactis, *Bifidobacterium longum* and *Bifidobacterium infantis*, in particular, the composition may include a probiotic combination comprising or, alternatively, consisting of *Lactobacillus plantarum* PBS067 in combination with a strain of *Bifidobacterium lactis* BL050, *Bifidobacterium longum* BLG240 and *Bifidobacterium infantis* BI221.

An object of the present invention is a probiotic combination comprising:
- a) at least one strain belonging to the genus *Lactobacillus* selected from the species *Lactobacillus plantarum*; and
- c) at least one strain belonging to the genus *Bifidobacterium* selected from the species *Bifidobacterium* lactis, *Bifidobacterium* longum, *Bifidobacterium infantis*; wherein said probiotic combination includes or, alternatively, consists of: a strain of *Lactobacillus plantarum* PBS067 in combination with a strain of *Bifidobacterium lactis* BL050, *Bifidobacterium longum* BLG240 and *Bifidobacterium infantis* BI221; wherein said combination is for use in the prevention and/or treatment of chronic inflammatory bowel disease.

An object of the present invention is a composition comprising said probiotic combination and, optionally, pharmaceutical or food grade additives and excipients; wherein said probiotic combination comprises:
- a) at least one strain belonging to the genus *Lactobacillus* selected from the species *Lactobacillus plantarum*; and
- c) at least one strain belonging to the genus *Bifidobacterium* selected from the species *Bifidobacterium* lactis, *Bifidobacterium* longum, *Bifidobacterium infantis*; wherein said probiotic combination comprises or, alternatively, consists of: a strain of *Lactobacillus plantarum* PBS067 in combination with a strain of *Bifidobacterium lactis* BL050, *Bifidobacterium longum*

BLG240 and *Bifidobacterium infantis* BI221; and wherein said composition is for use in the prevention and/or treatment of chronic inflammatory bowel disease.

Preferably, said probiotic combination and said composition comprising said probiotic combination are both for use in a method for the prevention and/or treatment of chronic inflammatory bowel disease (IBD) selected from Crohn's disease and ulcerative colitis.

A preferred composition for use according to the invention comprises a probiotic combination comprising: a strain of *Lactobacillus helveticus* and a strain of *Bifidobacterium breve*, in particular the composition may include a probiotic combination comprising *Lactobacillus helveticus* LH060 and *Bifidobacterium breve* BB077.

According to a second preferred aspect of the invention, the compositions comprise a probiotic combination comprising:

a) at least one strain of the genus *Lactobacillus* selected from the species *Lactobacillus plantarum, Lactobacillus acidophilus, Lactobacillus helveticus* and *Lactobacillus* gasseri; and b) at least one other strain belonging to the genus *Lactobacillus* selected from the species *Lactobacillus rhamnosus, Lactobacillus reuteri* and *Lactobacillus fermentum;* in the prevention and/or treatment of gastrointestinal disorders.

A preferred composition for use according to the invention comprises a probiotic combination comprising: a strain of *Lactobacillus acidophilus* and a strain of *Lactobacillus reuteri*, in particular the composition may comprise a probiotic combination comprising *Lactobacillus acidophilus* PBS066 and *Lactobacillus reuteri* PBS072.

Another preferred composition for use according to the invention comprises a probiotic combination comprising: a strain of *Lactobacillus* gasseri and a strain of *Lactobacillus fermentum*, in particular the composition may comprise a probiotic combination comprising *Lactobacillus* gasseri LG050 and *Lactobacillus fermentum* PBS073.

According to a third preferred aspect of the invention, the compositions comprise a probiotic combination comprising:

a) at least one strain of the genus *Lactobacillus* selected from the species *Lactobacillus plantarum, Lactobacillus acidophilus, Lactobacillus helveticus* and *Lactobacillus* gasseri; and b) at least one other strain belonging to the genus *Lactobacillus* selected from the species *Lactobacillus rhamnosus, Lactobacillus reuteri* and *Lactobacillus fermentum;* and c) at least one strain belonging to the genus *Bifidobacterium* selected from the species *Bifidobacterium* lactis, *Bifidobacterium* breve, *Bifidobacterium* longum, *Bifidobacterium infantis*; in the prevention and/or treatment of gastrointestinal disorders.

A preferred composition for use according to the invention comprises a probiotic combination comprising: a strain of *Lactobacillus acidophilus*, a strain of *Lactobacillus reuteri* and a strain of *Bifidobacterium breve*, in particular the composition may comprise a probiotic combination comprising *Lactobacillus acidophilus* PBS066, *Lactobacillus reuteri* PBS072 in association with *Bifidobacterium breve* BB077.

Another preferred composition for use according to the invention comprises a probiotic combination comprising: a strain of *Lactobacillus helveticus*, a strain of *Lactobacillus rhamnosus* and a strain of *Bifidobacterium lactis*, in particular the composition may comprise a probiotic combination comprising *Lactobacillus helveticus* LH060, *Lactobacillus rhamnosus* LRH020 in association with *Bifidobacterium lactis* BL050.

*Lactobacillus plantarum* (*L. plantarum* or LP) strain called "PBS067" was deposited at the Leibniz-Institut DSMZ-Deutsche Sammlung von Mikroorganismen und Zellkulturen GmbH, under the Budapest Treaty, on 17 Jun. 2011, under the Accession Number "DSM 24937".

*Lactobacillus acidophilus* (*L. acidophilus* or LA) strain called "PBS066" was deposited at the DSMZ—Deutsche Sammlung von Mikroorganismen und Zellkulturen GmbH, under the Budapest Treaty, on 17 Jun. 2011, under the Accession Number "DSM 24936".

*Lactobacillus rhamnosus* (*L. rhamnosus* or LRH) strain called "LRH020" was deposited at the Leibniz-Institut DSMZ-Deutsche Sammlung von Mikroorganismen und Zellkulturen GmbH, under the Budapest Treaty, on 17 Jan. 2012, under the Accession Number "DSM 25568".

*Lactobacillus reuteri* (*L. reuteri* or LR) strain called "PBS072" was deposited at the DSMZ—Deutsche Sammlung von Mikroorganismen und Zellkulturen GmbH, under the Budapest Treaty, on 14 Sep. 2011, under Accession Number "DSM 25175".

*Lactobacillus helveticus* (*L. helveticus* o LH) strain called "LH060" was deposited at the BCCM (Belgian Coordinated Collections of Micro-organisms)—LMG (Laboratorium voor Microbiologie—Bacteriënverzamelig, under the Budapest Treaty, on 9 Apr. 2019, under the Accession number "LMG P-31392.

*Lactobacillus* gasseri (*L. gasseri* o LG) strain called "LG050" was deposited at the BCCM (Belgian Coordinated Collections of Micro-organisms)—LMG (Laboratorium voor Microbiologie—Bacteriënverzamelig), under the Budapest Treaty on 24 May 2016, under the Accession number "LMG P-29638".

*Lactobacillus fermentum* (*L. fermentum* o LF) strain called "PBS073" was deposited at the DSMZ—DeutscheSammlung von Mikroorganismen und Zellkulturen GmbH, under the Budapest Treaty, on 14 Sep. 2011, under the Accession number "DSM 251576".

*Bifidobacterium lactis* (*B. lactis* o BL) strain called "BL050" was deposited at the DSMZ—DeutscheSammlung von Mikroorganismen und Zellkulturen GmbH, under the Budapest Treaty, on 17 Jan. 2012, under the Accession number "DSM 25566".

*Bifidobacterium breve* (*B. breve* o BB) strain called "BB077" was deposited at the BCCM (Belgian Coordinated Collections of Micro-organisms)—LMG (Laboratorium voor Microbiologie—Bacteriënverzamelig), under the Budapest Treaty, on 9 Jan. 2017, under the Accession number "LMG P-30157".

*Bifidobacterium longum* (*B. longum* o BLG) strain called "BLG240" was deposited at the BCCM (Belgian Coordinated Collections of Micro-organisms)—LMG (Laboratorium voor Microbiologie—Bacteriënverzamelig), under the Budapest Treaty on Aug. 4, 2016, under the Accession number "LMG P-29511".

*Bifidobacterium infantis* (*B. infantis* o BI) strain called "BI221" was deposited at the BCCM (Belgian Coordinated Collections of Micro-organisms)—LMG (Laboratorium voor Microbiologie—Bacteriënverzamelig), under the Budapest Treaty, on 24 May 2016 under the Accession number "LMG P-29639".

This invention relates to the use of compositions comprising a probiotic combination as above defined, as an active ingredient, and at least a physiologically acceptable excipient and/or vehicle.

The compositions of the invention can be formulated by conventional methods. Preferred forms of administration are solid formulations, such as rigid capsules, single or coupled sachets, sticks, oro-soluble sticks, tablets, granulates, or liquid formulations, such as bottles with mono-dosing or multi-dosing cap, multi-dose dispersions in oily phase, drops, syrups, multi-phase emulsions, etc.

*Lactobacillus plantarum* (LP), preferably the *Lactobacillus plantarum* PBS067 strain, may be present in the composition, as a percentage by weight based on the total weight of the probiotic combination, from 1% to 25%, preferably from 5% to 15%, even more preferably it is equal to 8%.

*Lactobacillus plantarum* (LP), preferably the *Lactobacillus plantarum* PBS067 strain, may be present in each individual unit dose in amounts ranging from 0.5 to 3 billion UFC, preferably in amounts ranging from 1 to 2 billion UFC, more preferably it is present in an amount equal to 1 billion UFC.

*Lactobacillus acidophilus* (LA), preferably the *Lactobacillus acidophilus* PBS066 strain, may be present in the composition, as a percentage by weight based on the total weight of the probiotic combination, from 20% to 80%, preferably from 30% to 70%, even more preferably it is equal to 38% and 50%.

*Lactobacillus acidophilus* (LA), preferably the *Lactobacillus acidophilus* PBS066 strain, may be present in each individual unit dose in amounts ranging from 0.5 to 6 billion UFC, preferably in amounts ranging from 1 to 4 billion UFC, more preferably it is present in an amount equal to 2 billion UFC.

*Lactobacillus rhamnosus* (LRH), preferably the *Lactobacillus rhamnosus* LRH020 strain, may be present in the composition, as a percentage by weight based on the total weight of the probiotic combination, from 15% to 80%, preferably from 20% to 70%, even more preferably it is equal to 29%.

*Lactobacillus rhamnosus* (LRH), preferably the *Lactobacillus rhamnosus* LRH020 strain, may be present in each individual unit dose in amounts ranging from 0.5 to 6 billion UFC, preferably in amounts ranging from 1 to 4 billion UFC, more preferably it is present in an amount equal to 2 billion UFC.

*Lactobacillus reuteri* (LR), preferably the *Lactobacillus reuteri* PBS072 strain, may be present in the composition, as a percentage by weight based on the total weight of the probiotic combination, from 20% to 80%, preferably from 30% to 70%, even more preferably it is equal to 38% and 50%.

*Lactobacillus reuteri* (LR), preferably the *Lactobacillus reuteri* PBS072 strain, may be present in each individual unit dose in amounts ranging from 0.5 to 6 billion CFU, preferably in amounts ranging from 1 to 4 billion CFU, more preferably it is present in an amount equal to 2 billion CFU.

*Lactobacillus helveticus* (LH), preferably the *Lactobacillus helveticus* LH060 strain, may be present in the composition, as a percentage by weight based on the total weight of the probiotic combination, from 15% to 90%, preferably from 30% to 70%, even more preferably it is equal to 43% and 60%.

*Lactobacillus helveticus* (LH), preferably the *Lactobacillus helveticus* LH060 strain, may be present in each individual unit dose in amounts ranging from 0.5 to 6 billion CFU, preferably in amounts ranging from 1 to 4 billion UFC, more preferably it is present in an amount equal to 2 billion CFU.

*Lactobacillus* gasseri (LG), preferably the *Lactobacillus* gasseri LG050 strain, may be present in the composition, as a percentage by weight based on the total weight of the probiotic combination, from 30% to 70%, preferably from 40% to 60%, even more preferably it is equal to 50%.

*Lactobacillus* gasseri (LG), preferably the *Lactobacillus* gasseri LG050 strain, may be present in each individual unit dose in amounts ranging from 0.5 to 6 billion CFU, preferably in amounts ranging from 1 to 4 billion UFC, more preferably it is present in an amount equal to 2 billion CFU.

*Lactobacillus fermentum* (LF), preferably the *Lactobacillus fermentum* PBS073 strain, may be present in the composition, as a percentage by weight based on the total weight of the probiotic combination, from 30% to 70%, preferably from 40% to 60%, even more preferably it is equal to 50%.

*Lactobacillus fermentum* (LF), preferably the *Lactobacillus fermentum* PBS073 strain, may be present in each individual unit dose in amounts ranging from 0.5 to 6 billion CFU, preferably in amounts ranging from 1 to 4 billion CFU, more preferably it is present in an amount equal to 2 billion CFU.

*Bifidobacterium lactis* (BL), preferably the *Bifidobacterium lactis* BL050 strain, may be present in the composition, as a percentage by weight based on the total weight of the probiotic combination, from 10% to 60%, preferably from 20% a 40%, even more preferably it is equal to 13% e 30%.

*Bifidobacterium lactis* (BL), preferably the *Bifidobacterium lactis* BL050 strain, may be present in each individual unit dose in amounts ranging from 0.5 to 6 billion CFU, preferably in amounts ranging from 1 to 4 billion CFU, more preferably it is present in an amount equal to 1 billion CFU and 2 billion CFU.

*Bifidobacterium breve* (BB), preferably the *Bifidobacterium breve* BB077 strain, may be present in the composition, as a percentage by weight based on the total weight of the probiotic combination, from 10% to 80%, preferably from 20% to 60%, even more preferably it is equal to 25% and 40%.

*Bifidobacterium breve* (BB), preferably the *Bifidobacterium breve* BB077 strain, may be present in every individual unit dose in amounts ranging from 0.5 to 6 billion CFU, preferably in amounts ranging from 1 to 4 billion CFU, more preferably it is present in an amount equal to 2 billion CFU.

*Bifidobacterium longum* (BLG), preferably the *Bifidobacterium longum* BLG240 strain, may be present in the composition, as a percentage by weight based on the total weight of the probiotic combination, from 20% to 80%, preferably from 30% to 70%, even more preferably it is equal to 40%.

*Bifidobacterium longum* (BLG), preferably the *Bifidobacterium longum* BLG240 strain, may be present in each individual unit dose in amounts ranging from 0.5 to 6 billion CFU, preferably in amounts ranging from 1 to 4 billion CFU, more preferably it is present in an amount equal to 1 billion UFC.

*Bifidobacterium infantis* (BI), preferably the *Bifidobacterium infantis* BI221 strain, may be present in the composition, as a percentage by weight based on the total weight of the probiotic combination, from 20% to 80%, preferably from 30% to 70%, even more preferably it is equal to 40%.

*Bifidobacterium infantis* (BI), preferably the *Bifidobacterium infantis* BI221 strain, may be present in each individual unit dose in amounts ranging from 0.5 to 6 billion CFU, preferably in amounts ranging from 1 to 4 billion CFU, more preferably it is present in an amount equal to 1 billion CFU.

The species present in the probiotic combination, as reported in Example 1, may be present in a weight ratio of 0.7:0.7:1 or 1:1:1 ratio when expressed in CFU.

The species present in the probiotic combination, as reported in Example 2, may be present in a weight ratio of 1:1.5:1 or 1:1:1 ratio when expressed in CFU.

The species present in the probiotic combination, as reported in Example 3, may be present in a weight ratio of 1:1 or 1:1 ratio when expressed in CFU.

The species present in the probiotic combination, as reported in Example 4, may be present in a weight ratio of 1:1 or 1:1 ratio when expressed in CFU.

The species present in the probiotic combination, as reported in Example 5, may be present in a weight ratio of 0.7:1: or 1:1 ratio when expressed in CFU.

It is an object of this invention a probiotic combination comprising or, alternatively, consisting of: *L. plantarum* PBS067, *B. lactis* BL050, *B. infantis* BI221 and *B. longum* BLG240; preferably said combination is present together with pharmaceutical or food grade additives and/or excipients selected from fibres, prebiotic fibres such as inulin or FOS (Fructo-oligosaccharides) or maltodextrins, vitamins such as a vitamin of the B group, such as vitamin B6. Preferably, an exemplary embodiment of the composition of this invention is given in Example 6. Preferably, the composition of Example 6 is useful in preventing and/or treating chronic inflammatory bowel diseases (IBD) selected from Crohn's disease and rettocolitis/ulcerative colitis.

The species present in the probiotic combination, as reported in Example 6, may be present in a weight ratio of 1:1.7:5:5 or 1:1:1:1 ratio when expressed in CFU.

The probiotic compositions of the invention can be administered orally.

According to a preferred aspect of the invention, the compositions of the invention are useful in the prevention and/or treatment of the following gastrointestinal disorders:

intestinal dysbiosis;

inflammatory, acute or chronic diseases of the digestive system, such as chronic inflammatory bowel diseases such as Crohn's disease or rettocolitis/ulcerative colitis, or peptic diseases, esophagitis, diverticulitis;

enterocolitis, infectious enterocolitis caused by microorganisms;

diarrhoea, in particular diarrhoea caused by microorganisms: bacteria, viruses and parasites;

diarrhoea from food intolerance, such as gluten and/or lactose intolerance; diarrhoea from procynthetic drugs able to selectively stimulate the motor function of the intestine (motiline agonists), for example antibiotics such as erythromycin;

impaired nutrient absorption resulting in, for example, intestinal malabsorption.

According to an additional preferred aspect of the invention, the compositions of the invention are useful as intestinal antiperistaltic.

The probiotic strains of the invention's compositions can promote proper intestinal function by supporting nutrient absorption.

Further object of this invention are compositions comprising a probiotic combination comprising:

*Lactobacillus* gasseri LG050 and *Lactobacillus fermentum* PBS073, or

*Lactobacillus acidophilus* PBS066 and *Lactobacillus reuteri* PBS072;

or

*Lactobacillus acidophilus* PBS066, *Lactobacillus reuteri* PBS072 in association with *Bifidobacterium breve* BB077;

or

*Lactobacillus helveticus* LH060, *Lactobacillus rhamnosus* LRH020 in association with *Bifidobacterium lactis* BL050;

or

*Lactobacillus helveticus* LH060 and *Bifidobacterium breve* BB077;

and their use as a medicament.

The following examples further illustrate the invention.

EXAMPLES

Formulative Examples

Example 1

A composition in oro-soluble stick form has been prepared, containing:

TABLE 1

| INGREDIENTS | % wt/wt | BILLION/DOSE |
|---|---|---|
| *L. acidophilus* PBS066 | 2.75 | 2 |
| *L. reuteri* PBS072 | 2.75 | 2 |
| *B. breve* BB077 | 1.65 | 2 |
| FOS 93% | 7.2 | — |
| Inulin 90% | 7.2 | — |
| Folic acid | 0.003 | — |
| Vitamin B12 | 0.035 | — |
| Vitamin B6 | 0.022 | — |
| Sorbitol | 55 | — |
| Silicon dioxide | 1 | — |
| Maltodextrin | 22.39 | — |

Example 2

A composition in capsule form has been prepared, containing:

TABLE 2

| INGREDIENTS | % wt/wt | BILLION/DOSE |
|---|---|---|
| *L. rhamnosus* LRH020 | 1.11 | 2 |
| *L. helveticus* LH060 | 1.11 | 2 |
| *B. lactis* BL050 | 0.733 | 2 |
| Vitamin B12 | 0.035 | — |
| Vitamin B6 | 0.022 | — |
| Corn starch | 49 | — |
| Magnesium stearate | 2 | |
| Silicon dioxide | 1 | — |
| Maltodextrin | 44.99 | — |

Example 3

A composition in stick form has been prepared, containing:

TABLE 3

| INGREDIENTS | % wt/wt | BILLION/DOSE |
|---|---|---|
| *L. gasseri* LG050 | 1.25 | 2 |
| *L. fermentum* PBS073 | 1.25 | 2 |
| Acacia fibre | 55 | — |
| Aroma | 0.08 | — |

TABLE 3-continued

| INGREDIENTS | % wt/wt | BILLION/DOSE |
|---|---|---|
| Vitamin B6 | 0.022 | — |
| Sucralose | 35 | — |
| Silicon dioxide | 1 | — |
| Maltodextrin | 6.398 | — |

Example 4

A composition in drops form has been prepared, containing:

TABLE 4

| INGREDIENTIS | % wt/wt | BILLION/DOSE |
|---|---|---|
| *L. acidophilus* PBS066 | 0.2306 | 2 |
| *L. reuteri* PBS072 | 0.2306 | 2 |
| Silicon dioxide | 0.0264 | — |
| Maltodextrin | 2.1476 | — |
| MCT | 96.9711 | — |
| E461 | 0.1959 | — |
| Vitamin E | 0.1959 | — |
| Tocopherols Mix | 0.0020 | — |

Example 5

A composition in capsule form has been prepared, containing:

TABLE 5

| INGREDIENTS | % wt/wt | BILLION/DOSE |
|---|---|---|
| *L. helveticus* LH060 | 1.11 | 2 |
| *B. breve* BB077 | 0.733 | 2 |
| Corn starch | 40 | — |
| Folic Acid | 0.003 | — |
| Vitamin B12 | 0.035 | — |
| Magnesium stearate | 2 | — |
| Silicon dioxide | 1 | — |
| Maltodextrin | 55.119 | — |

Example 6

A composition in sachet form has been prepared, containing:

TABLE 6

| INGREDIENTIS | % wt/wt | BILLION/DOSE |
|---|---|---|
| *L. plantarum* PBS067 | 1.25 | 1 |
| *B. lactis* BL050 | 1.25 | 1 |
| *B. infantis* BI221 | 1.375 | 1 |
| *B. longum* BLG240 | 2 | 1 |
| FOS | 68 | — |
| Aroma | 1.25 | — |
| Vitamin B6 | 0.022 | — |
| Sucralose | 0.08 | — |
| Silicon dioxide | 1 | — |
| Maltodextrin | 23.773 | — |

Experimental Examples

The following experimental examples are related to the evaluation of the efficacy of the compositions of the invention in the prevention and/or treatment of gastrointestinal disorders.

Example 7

A clinical study was conducted to determine the efficacy of the composition of Example 6 compared to the placebo formulation in Table 7 in preventing and/or treating chronic inflammatory bowel disease (IBD).

Methods

A double-blind, placebo-controlled randomized trial was conducted on 50 elder subjects aged between 60 and 80 years. The subjects were randomly divided into two groups and assigned either the active product, namely the composition of Example 6 according to the invention, or the placebo product to be taken for 28 consecutive days followed by a period of 28 days of wash-out.

TABLE 7

| INGREDIENTIS | % wt/wt |
|---|---|
| FOS | 68 |
| Aroma | 1.25 |
| Vitamin B6 | 0.022 |
| Sucralose | 0.08 |
| Silicon dioxide | 1 |
| Maltodextrin | 2.648 |

Before the beginning of treatment (T0), at the end of treatment (T28) and at the end of the wash-out period (T56), stool samples were taken from subjects for the determination of faecal markers (calprotectin and β-defensin 2) and for the analysis of the intestinal microbiota.

Fecal Markers Analysis

The results were obtained by the dosage of calprotectin and μ-defensin 2.

Fecal calprotectin is a non-invasive marker for the diagnosis of chronic inflammatory intestinal diseases allowing a direct correlation. High levels of fecal calprotectin indicate the migration of neutrophils to the intestinal mucosa, which occurs during intestinal inflammation, including inflammation caused by inflammatory bowel disease, IBD. The level of calprotectin is generally very high in patients suffering from chronic inflammatory bowel diseases, such as Crohn's disease or disease, ulcerative colitis. An increase in calprotectin values can also be observed in all inflammatory, acute or chronic diseases, limited to the digestive tract, such as peptic diseases, esophagitis, diverticulitis and infectious or toxic enterocolitis.

The levels of calprotectin in the subjects of the active group were normal values throughout the treatment (below 45 μg/gr). Similar results were also observed for placebo subjects, although the percentages of subjects were lower than the active group.

Figure 1:
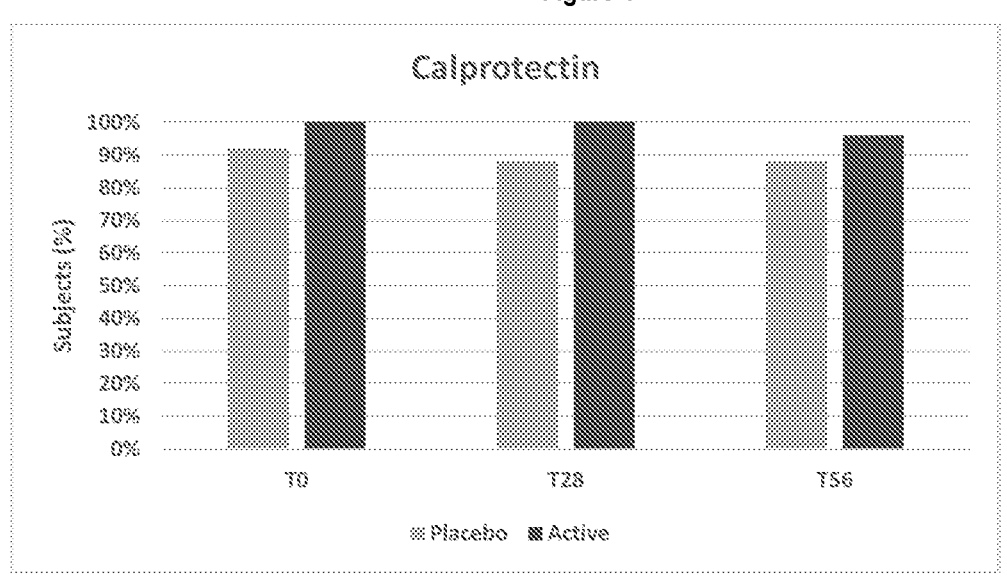
FIG. 1 shows the percentage of subjects, in both the active and placebo groups, with calprotectin values below 45 μg/g for the three checkpoints.

FIG. 1 shows the percentages of subjects with faecal levels below 45 μg/g for the three study times.

Fecal β-defensin 2 levels increased in both groups, within the active group the values increased significantly when compared to placebo as shown in FIG. 2.

The values of fecal β-Defensin-2 were measured at the beginning of treatment (T0), at the end of treatment (T28) and at the end of the wash-out period (T56).

As the main outcome of the study, fecal markers (calprotectin and β-defensin-2) were selected to follow the course of inflammation in subjects with gastrointestinal problems. The results showed a significant increase in β-defensin-2 during the follow-up period compared to the beginning of treatment and stable levels of calprotectin throughout the study.

Gut Microbiota Analysis

Following the analysis of the gut microbiota by the extraction of microbial DNA from faecal samples, 12 phyla, 21 classes, 54 orders, 107 families and 248 genera were detected.

The dominant phyla present in the samples belong to *Firmicutes* and *Bacteroida* followed by the Proteobacteria, Verrucomicrobia and Actinobacteria. Changes in biodiversity in terms of species abundance within each group were also evaluated for the different checkpoints. At the end of the treatment T28, a positive change in the genera *Escherichia-Shigella, Acidaminococcus* and *Akkermansia* was observed for placebo, while a negative change in the following genera *Faecalibacterium, Lachnospira, Roseburia* and *Butyricicoccus* was observed, necessary to have a microbiota in equilibrium.

In contrast, the active group at the end of treatment experienced a positive change in genera with a positive influence on the intestinal microbiota including *Dialister, Lachnospira, Bifidobacterium* and *Lachnoclostridium,* while the genera that have undergone a negative variation we find *Parabacteroidetes* and *Chlostridium.*

At the end of the wash-out period the same trend was maintained: the active group experienced a positive change in genera such as *Butyricicoccus* and *Akkermansia,* known to have a positive impact on the intestinal microbiota; while for the placebo group a negative change in the following genera was observed: *Bifidobacterium, Blautia, Lactobacillus* and *Faecalibacterium.*

Example 8

In vitro studies have been carried out to determine the ability of the strains of the invention to produce antimicrobial cytokines and peptides and to exert direct antimicrobial action on microorganisms. The results are shown in Table 8 to 17.

TABLE 8

| Sample | Run1 | Run2 | Mean | Standard deviation | t-Test | Statistics |
|---|---|---|---|---|---|---|
| CTR– | 15.72 | 15.79 | 15.76 | 0.05 | 0.001 | |
| CTR+ | 26.45 | 27.23 | 26.84 | 0.55 | 1.000 | |
| LA - PBS066 | 26.02 | 24.87 | 25.45 | 0.82 | 0.183 | |
| LP -PBS067 | 24.30 | 23.52 | 23.91 | 0.55 | 0.034 | * |
| BL - BL050 | 24.96 | 24.49 | 24.73 | 0.33 | 0.043 | * |
| BI - BI221 | 24.16 | 26.27 | 25.21 | 1.49 | 0.285 | |
| BLG - BLG240 | 18.85 | 18.50 | 18.68 | 0.25 | 0.003 | * |

TABLE 9

Beta Defensin 2 (DEFB2 pg/ml)

| Sample | Run1 | Run2 | Run3 | Mean | Standard deviation | t-Test vs Ctr+ | Statistics |
|---|---|---|---|---|---|---|---|
| CTR– | 6.21 | 3.64 | 2.86 | 4.68 | 1.60 | | |
| | 5.93 | 6.21 | 3.20 | | | | |
| CTR+ | 5.32 | 4.83 | 4.98 | 5.18 | 0.29 | | |
| | 5.21 | 5.08 | 5.65 | | | | |
| LA - PBS066 | 6.44 | 6.10 | 5.42 | 5.99 | 0.52 | 0.017 | * |
| LP - PBS067 | 5.99 | 4.87 | 4.70 | 5.19 | 0.70 | 0.977 | |
| BL - BL050 | 6.03 | 5.94 | 5.99 | 5.99 | 0.05 | 0.002 | * |
| BI - BI221 | 5.22 | 4.87 | 5.82 | 5.30 | 0.48 | 0.633 | |
| BLG - BLG240 | 6.44 | 5.99 | 3.20 | 5.21 | 1.76 | 0.969 | |

TABLE 10

Cathelicidin Antimicrobial Peptides (CAMPs pg/ml)

| Sample | Run1 | Run2 | Run3 | Mean | Standard deviation | t-Test vs Ctr+ | Statistics |
|---|---|---|---|---|---|---|---|
| CTR– | 8.10 | 13.60 | 14.20 | 11.90 | 2.42 | | |
| | 13.50 | 12.10 | 9.90 | | | | |
| CTR+ | 14.32 | 13.45 | 11.83 | 12.63 | 1.41 | | |
| | 11.18 | 11.15 | 13.82 | | | | |
| LA - PBS066 | 15.77 | 14.69 | 14.01 | 14.82 | 0.89 | 0.045 | * |
| LP - PBS067 | 10.6 | 13.5 | 15.9 | 13.33 | 2.65 | 0.605 | |
| BL - BL050 | 14.63 | 16.52 | 15.75 | 15.63 | 0.95 | 0.013 | * |
| BI - BI221 | 12.35 | 14.56 | 11.12 | 12.68 | 1.74 | 0.963 | |
| BLG - BLG240 | 12.44 | 13.11 | 13.07 | 12.87 | 0.38 | 0.779 | |

TABLE 11

*Enterococcus faecalis*

| Time | 0 Log CFU/mL | 3 Log CFU/mL | 6 Log CFU/mL | 24 Log CFU/mL |
|---|---|---|---|---|
| LA - PBS066 | 5.11 | 4.37 | 4.49 | 3.7 |
| LF - PBS073 | 5.11 | 5.14 | 6.17 | 7.92 |
| LP - PBS067 | 5.11 | 4.7 | 4 | 4.7 |
| LR - PBS072 | 5.11 | 5.16 | 6.22 | 8.32 |
| LRh - LRH020 | 5.11 | 5.48 | 6.3 | 8.04 |
| BL - BL050 | 5.11 | 6.17 | 8.17 | 8.44 |
| BLg - BLG240 | 5.11 | 6.3 | 6.78 | 8.9 |
| BI - BI221 | 5.11 | 6.63 | 6.86 | 7.84 |
| Control | 5.11 | 6.54 | 7.92 | 9.16 |

TABLE 12

| S. enteritidis | |
| --- | --- |
| | log CFU/ml |
| LG - LG050 | 6.98 |
| LA - PBS066 | 6.99 |
| LP - PBS067 | 3.23 |
| LR - PBS072 | 9.00 |
| LRh - LRH020 | 1.70 |
| BL - BL050 | 1.60 |
| BI - BI221 | 1.36 |
| BB - BB077 | 9.00 |
| LF - PBS073 | 1.54 |
| LH - LHO | 1.75 |
| Ctrl | 9.00 |

TABLE 13

| L. monocytogenes | |
| --- | --- |
| | log CFU/ml |
| LG - LG050 | 5.30 |
| LA - PBS066 | 5.48 |
| LP - PBS067 | 4.45 |
| LR - PBS072 | 8.54 |
| LRh - LRH020 | 4.40 |
| BL - BL050 | 5.61 |
| BI - BI221 | 6.08 |
| BB - BB077 | 8.54 |
| LF - PBS073 | 6.20 |
| LH-LH060 | 6.18 |
| Ctrl | 8.54 |

TABLE 14

| S. typhimurium | |
| --- | --- |
| | log CFU/ml |
| LG - LG050 | 2.70 |
| LA - PBS066 | 3.98 |
| LP - PBS067 | 3.83 |
| LR - PBS072 | 9.06 |
| LRh - LRH020 | 4.48 |
| BL - BL050 | 4.90 |
| BI - BI221 | 3.48 |
| BB - BB077 | 9.06 |
| LF - PBS073 | 2.48 |
| LH - LH060 | 3.40 |
| Ctrl | 9.06 |

TABLE 15

| C. difficile | |
| --- | --- |
| 48 h | Log10 (CFU/ml) |
| LG - LG050 | 7.30 |
| LA - PBS066 | 2.18 |
| LP - PBS067 | 0.18 |
| LR - PBS072 | 2.90 |
| LRh - LRH020 | 1.95 |
| BL - BL050 | 7.00 |
| BI - BI221 | 7.08 |
| BB - BB077 | 7.28 |
| LF - PBS073 | 3.70 |
| LH - LH060 | 1.48 |
| Ctrl | 7.06 |

TABLE 16

| H. pylori | | | |
| --- | --- | --- | --- |
| | Supernatant concentration (% v/v) | | |
| | 0.05 (% v/v) | 0.1 (% v/v) | 0.2 (% v/v) |
| LG - LG050 | 1.28 | 0.07 | 0.05 |
| LA - PBS066 | 1.28 | 0.78 | 0.03 |
| LP - PBS067 | 1.15 | 0.04 | 0.06 |
| LR - PBS072 | 1.25 | 1.2 | 0.65 |
| LRh - LRH020 | 0.02 | 0.03 | 0.01 |
| BL - BL050 | 0.03 | 0.02 | 0.02 |
| BI - BI221 | 0.04 | 0.02 | 0.02 |
| BB - BB077 | 1.31 | 1.26 | 0.74 |
| LF - PBS073 | 0.82 | 0.03 | 0.05 |
| LH - LH060 | 0.73 | 0.06 | 0.04 |
| Ctrl | | 1.29 | |

TABLE 17

| ANTIMICROBIAL ACTIVITY BY CONTACT (DIRECT INHIBITION) | | | | | |
| --- | --- | --- | --- | --- | --- |
| Strain | E. faecalis | S. enteriditis | S. typhimurium | C. jejuni | L. mono-cytogenes |
| LA - PBS066 | ** | — | * | ** | — |
| LF - PBS073 | — | ** | * | ** | — |
| LP - PBS067 | ** | * | * | ** | — |
| LR - PBS072 | ** | — | — | ** | — |
| LH - LH060 | n.d. | ** | — | ** | — |
| LG - LG050 | n.d. | — | * | — | — |
| LRh - LRH020 | ** | ** | — | — | — |
| BL - BL050 | ** | ** | — | ** | — |
| BLg - BLG240 | ** | n.d. | n.d. | n.d. | n.d. |
| BI - BI221 | — | ** | * | ** | — |
| BB - BB077 | n.d. | — | — | — | — |

***synergy
**strong inhibition
*moderate/significant inhibition
— no inhibition
n.d. not determined Example 9

In vitro studies have been carried out to determine the efficacy of the invention strains in diarrhea caused by food intolerance, thanks to their action on gliadin metabolism and lactase activity. The results are shown in Table 18 and 19.

TABLE 18

| Lactose digestion - lactase like activity | | |
| --- | --- | --- |
| | 4 h | 8 h |
| LP - PBS067 | 29.7 | 18.8 |
| LG - LG050 | 28.9 | 11.8 |
| BI - BI221 | 18.6 | 7.2 |
| BLg - BLG240 | 14.2 | 7.5 |
| BB - BB077 | 13.3 | 8.5 |
| BL - BL050 | 29.6 | 15.6 |
| LF - PBS073 | 26.6 | 8.9 |
| LH - LH060 | 6.1 | 2 |
| LR - PBS072 | 19.3 | 6.8 |
| LRh - LRH020 | 29.9 | 16.9 |
| Lactose 30 ug | 30 | 30 |

TABLE 19

| Gliadin metabolism | | |
| --- | --- | --- |
| | 4 h | 8 h |
| LP - PBS067 | 39.8 | 34.7 |
| LG - LG050 | 38.8 | 36.2 |
| BI - BI221 | 43 | 33 |
| BLg - BLG240 | 30.6 | 25.4 |
| BB - BB077 | 25.3 | 20.3 |
| BL - BL050 | 39.7 | 24.9 |
| LF - PBS073 | 35.5 | 26.6 |
| LH - LH060 | 32.5 | 22.9 |
| LR - PBS072 | 25.3 | 24.4 |
| LRh - LRH020 | 40.1 | 33.3 |
| Gliadin 50 ppm | 50 | 50 |

Example 10

An ex vitro study was carried out to determine the efficacy of the invention strains as intestinal antiperistaltic, measuring the ability to modulate interaction with the motilin receptor (erythromycin antagonist). The results are shown in Table 20 and 21.

TABLE 20

| Activation of motilin receptor in the presence of metabolites of probiotic strains | | | |
| --- | --- | --- | --- |
| | Mean | Ach nmoli/well st. dev. | % Var vs CTR+ |
| CTR− | 17.03 | 2.37 | — |
| LH - LH060 | 14.39 | 3.14 | −75% |
| BLg - BLG240 | 19.39 | 3.14 | −67% |
| BI - BI221 | 20.78 | 1.96 | −64% |
| LA - PBS066 | 25.78 | 4.32 | −56% |
| LF - PBS073 | 9.94 | 1.57 | −83% |
| LG - LG050 | 10.50 | 2.36 | −82% |
| LR - PBS072 | 14.94 | 1.57 | −74% |
| LRh - LRH020 | 27.44 | 1.96 | −53% |
| BB - BB077 | 13.56 | 5.11 | −77% |
| BL - BL050 | 44.67 | 1.18 | −23% |
| LP - PBS067 | 41.89 | 2.75 | −28% |
| CTR+ | 58.28 | 1.64 | |

TABLE 21

| Activation of motilin receptor in the presence of probiotic strains | | | |
| --- | --- | --- | --- |
| | Mean | Ach nmoli/well st. dev. | % Var vs CTR+ |
| CTR− | 17.03 | 2.37 | — |
| LH - LH060 | 11.61 | 4.71 | −80% |
| BLg - BLG240 | 1.89 | 0.39 | −97% |
| BI - BI221 | 8.56 | 0.39 | −85% |
| LA - PBS066 | 13.83 | 1.57 | −76% |
| LF - PBS073 | 7.72 | 2.36 | −87% |
| LG - LG050 | 0.78 | 1.18 | −99% |
| LR - PBS072 | 6.06 | 0.79 | −90% |
| LRh - LRH020 | 6.33 | 1.18 | −89% |
| BB - BB077 | 22.72 | 7.07 | −61% |
| BL - BL050 | 9.94 | 2.36 | −83% |
| LP - PBS067 | 10.78 | 9.04 | −82% |
| CTR+ | 58.28 | 1.64 | 2.422512235 |

Example 11

In vitro studies have been carried out to determine the efficacy of the strains of the invention as a support in the absorption of micronutrients such as calcium, iron, magnesium and folic acid. The results are shown in Table 22 to 25.

TABLE 22

| Calcium Absorption | | | |
| --- | --- | --- | --- |
| | T1H | T4H | T8H |
| CTR | 8.1% | 16.3% | 23.1% |
| LA - PBS066 | 12.9% | 25.4% | 36.0% |
| LF - PBS073 | 13.0% | 24.9% | 36.4% |
| LG - LG050 | 11.0% | 24.2% | 35.6% |
| LP - PBS067 | 13.6% | 25.8% | 33.2% |
| LH - LH060 | 12.1% | 24.0% | 35.4% |
| LRh - LRH020 | 13.2% | 25.4% | 35.6% |
| LR - PBS072 | 8.4% | 23.2% | 34.9% |
| BLg - BLG240 | 12.1% | 24.5% | 35.2% |
| BI - BI221 | 12.7% | 24.7% | 35.1% |
| BB - BB077 | 14.2% | 26.1% | 35.2% |
| BL - BL050 | 12.3% | 23.9% | 34.7% |

TABLE 23

| Iron absorption | | | |
| --- | --- | --- | --- |
| | T1H | T4H | T8H |
| CTR | 13.9% | 25.1% | 36.6% |
| LA - PBS066 | 17.8% | 31.9% | 43.5% |
| LF - PBS073 | 16.4% | 29.0% | 40.9% |
| LG - LG050 | 17.8% | 31.2% | 43.2% |
| LP - PBS067 | 15.8% | 29.6% | 41.9% |
| LH - LH060 | 14.5% | 27.1% | 37.2% |
| LRh - LRH020 | 16.2% | 27.6% | 37.6% |
| LR - PBS072 | 15.8% | 26.9% | 39.0% |
| BLg - BLG240 | 14.6% | 28.9% | 39.0% |
| BI - BI221 | 16.9% | 29.4% | 39.0% |
| BB - BB077 | 16.4% | 29.2% | 38.8% |
| BL - BL050 | 14.4% | 27.4% | 43.4% |

TABLE 24

| Magnesium Absorption | | | |
| --- | --- | --- | --- |
| | T1H | T4H | T8H |
| CTR | 11.1% | 22.1% | 31.9% |
| LA - PBS066 | 17.6% | 34.0% | 47.9% |
| LF - PBS073 | 16.6% | 33.4% | 47.8% |
| LG - LG050 | 16.8% | 33.5% | 48.7% |
| LP - PBS067 | 16.6% | 34.0% | 49.0% |
| LH - LH060 | 16.6% | 32.9% | 47.6% |
| LRh - LRH020 | 17.4% | 33.6% | 48.1% |
| LR - PBS072 | 17.3% | 33.3% | 47.8% |
| BLg - BLG240 | 16.9% | 33.8% | 47.7% |
| BI - BI221 | 17.6% | 34.1% | 47.9% |
| BB - BB077 | 17.1% | 32.5% | 45.7% |
| BL - BL050 | 16.6% | 31.7% | 45.5% |

TABLE 25

| Folic Acid absorption | | | |
| --- | --- | --- | --- |
| | T1H | T4H | T8H |
| CTR | 13.8% | 22.9% | 35.7% |
| LA - PBS066 | 28.8% | 51.1% | 59.1% |
| LF - PBS073 | 23.2% | 47.3% | 58.2% |
| LG - LG050 | 24.2% | 47.9% | 63.4% |
| LP - PBS067 | 23.2% | 51.1% | 65.2% |
| LH - LH060 | 23.1% | 44.7% | 57.0% |
| LRh - LRH020 | 28.0% | 48.5% | 60.2% |
| LR - PBS072 | 27.4% | 46.8% | 58.5% |

TABLE 25-continued

| Folic Acid absorption | | | |
| --- | --- | --- | --- |
| | T1H | T4H | T8H |
| BLg - BLG240 | 25.1% | 49.5% | 57.7% |
| BI - BI221 | 28.7% | 51.3% | 58.6% |
| BB - BB077 | 26.2% | 42.4% | 46.4% |
| BL - BL050 | 23.1% | 37.8% | 45.2% |

The invention claimed is:

1. A composition comprising a probiotic combination consisting of:
   a) at least one strain of the genus *Lactobacillus* selected from the species *Lactobacillus plantarum*; and
   c) at least one strain belonging to the genus *Bifidobacterium* selected from the species *Bifidobacterium lactis, Bifidobacterium longum,* and *Bifidobacterium infantis;*
   wherein said probiotic combination consists of:
   a strain of *Lactobacillus plantarum* PBS067 in combination with a strain of *Bifidobacterium lactis* BL050, *Bifidobacterium longum* BLG240 and *Bifidobacterium infantis* BI221.

2. The composition according to claim 1, wherein said probiotic combination consists of a strain of *Lactobacillus plantarum* PBS067 in combination with a strain of *Bifidobacterium lactis* BL050, *Bifidobacterium longum* BLG240 and *Bifidobacterium infantis* BI221, wherein said strains are present in a weight ratio of 1:1.7:5:5 or 1:1:1:1 ratio expressed in CFU.

3. The composition according to claim 1, wherein said composition is formulated for oral administration.

4. The composition according to claim 1, wherein said composition is as follows:

| INGREDIENTS | % wt/wt | BILLION/DOSE |
| --- | --- | --- |
| *L. plantarum* PBS067 | 1.25 | 1 |
| *B. lactis* BL050 | 1.25 | 1 |
| *B. infantis* BI221 | 1.375 | 1 |
| *B. longum* BLG240 | 2 | 1 |

-continued

| INGREDIENTS | % wt/wt | BILLION/DOSE |
| --- | --- | --- |
| FOS | 68 | — |
| Aroma | 1.25 | — |
| Vitamin B6 | 0.022 | — |
| Sucralose | 0.08 | — |
| Silicon dioxide | 1 | — |
| Maltodextrin | 23.773 | — |

5. A method for treating a chronic inflammatory bowel disease, comprising administering to a subject in need thereof a composition of claim 1.

6. The method of claim 5, wherein the subject has Crohn's disease or ulcerative colitis.

7. The method of claim 5, comprising administering to a subject in need thereof a composition wherein the probiotic combination consists of a strain of *Lactobacillus plantarum* PBS067 in combination with a strain of *Bifidobacterium lactis* BL050, *Bifidobacterium longum* BLG240 and *Bifidobacterium infantis* BI221.

8. The method of claim 7, wherein said strains are present in the composition in a weight ratio of 1:1.7:5:5 or 1:1:1:1 ratio expressed in CFU.

9. The method of claim 5, wherein in the composition is administered orally.

10. The method of claim 5, wherein in the composition comprises:

| INGREDIENTS | % wt/wt | BILLION/DOSE |
| --- | --- | --- |
| *L. plantarum* PBS067 | 1.25 | 1 |
| *B. lactis* BL050 | 1.25 | 1 |
| *B. infantis* BI221 | 1.375 | 1 |
| *B. longum* BLG240 | 2 | 1 |
| FOS | 68 | — |
| Aroma | 1.25 | — |
| Vitamin B6 | 0.022 | — |
| Sucralose | 0.08 | — |
| Silicon dioxide | 1 | — |
| Maltodextrin | 23.773 | — |

* * * * *